(12) United States Patent
Vallabhaneni

(10) Patent No.: US 10,697,005 B2
(45) Date of Patent: Jun. 30, 2020

(54) METHOD AND SYSTEM FOR TRACKING SPECIFIC IN SITU HYBRIDIZATIONS IN BIOLOGICAL SAMPLES USING MOLECULAR BARCODES

(71) Applicant: Ramesh Vallabhaneni, Orlando, FL (US)

(72) Inventor: Ramesh Vallabhaneni, Orlando, FL (US)

( * ) Notice: Subject to any disclaimer, the term of this patent is extended or adjusted under 35 U.S.C. 154(b) by 192 days.

(21) Appl. No.: 14/305,336

(22) Filed: Jun. 16, 2014

(65) Prior Publication Data

US 2015/0018231 A1    Jan. 15, 2015

Related U.S. Application Data

(60) Provisional application No. 61/839,645, filed on Jun. 26, 2013.

(51) Int. Cl.
*C12Q 1/68* (2018.01)
*C12Q 1/6841* (2018.01)

(52) U.S. Cl.
CPC .................. *C12Q 1/6841* (2013.01)

(58) Field of Classification Search
None
See application file for complete search history.

(56) References Cited

U.S. PATENT DOCUMENTS

| 7,943,304 B2 | 5/2011 | Vallabhaneni |
| 8,574,836 B2 | 11/2013 | Vallabhaneni |
| 2012/0142014 A1 | 6/2012 | Cai |

FOREIGN PATENT DOCUMENTS

WO    03052101 A1    6/2003

*Primary Examiner* — Frank W Lu
(74) *Attorney, Agent, or Firm* — David Guerra

(57) ABSTRACT

A method for tracking specific in situ hybridizations in biological samples using molecular barcodes is disclosed. Present invention specifically addresses the in suspension in situ hybridization protocols and makes it possible to track a mixed sample processed on a high throughput flow cytometer. Since the DNA probes selected for the molecular barcodes are naturally existing sequences on the chromosomes, each cell will have two copies of the molecular barcode as opposed to the single barcode provided by the other systems. Tracking is accomplished by following the florescence patterns emitted by the two, three, four or five fluorescent tags attached to the DNA probes. Alternatively, colorimetric system can be used for tracking by employing non-fluorescent tags and subsequent specific enzyme-substrate reactions.

11 Claims, 4 Drawing Sheets

METHOD AND SYSTEM FOR TRACKING SPECIFIC IN SITU HYBRIDIZATIONS IN BIOLOGICAL SAMPLES USING MOLECULAR BARCODES

CROSS-REFERENCE TO RELATED APPLICATION

This application is a U.S. non-provisional utility application under 35 U.S.C. § 111(a) based upon U.S. provisional application 61/839,645 filed on Jun. 26, 2013. Additionally, this U.S. non-provisional utility application claims the benefit of priority of U.S. provisional application 61/839,645 filed on Jun. 26, 2013. The entire disclosure of the prior application is incorporated herein by reference.

BACKGROUND OF THE INVENTION

1. Field of the Invention

The present invention relates to methods and systems to track specific in situ hybridizations in mixed biological samples. Specifically, the methods and systems disclosed herein relate to generation of molecular barcodes and tracking specific in situ hybridizations in mixed biological samples. More specifically, the methods and systems disclosed herein refer to the generation of molecular barcodes based on the fixed naturally occurring genomic sequences on a specific chromosome, which are different from the individual specific targets being investigated on a different chromosome; the methods and systems further involving separation of individual cells harboring specific in situ hybridization of specific genomic targets on a said chromosome, through high throughput flow cytometers reading the fluorescent signals generated from the molecular barcodes.

2. Description of the Prior Art

Tracking of individual cells which contain specific DNA hybridizations in a mixed biological sample is very difficult, especially when the mixed sample is processed for high throughput automation through flow cytometers. Yet, to maximize the speed afforded by these high throughput systems, multiple samples have to be mixed in small quantities.

Most of the molecular barcode systems currently available are developed for tracking cells attached to a solid surface. As such they don't address the unique requirements associated with a mixed sample processed in suspension on a high throughput flow cytometer.

Present invention specifically addresses the in suspension in situ hybridization protocols and makes it possible to track a mixed sample processed on a high throughput flow cytometer. Since the DNA probes selected for the molecular barcodes are naturally existing sequences on a given chromosome, and since each cell will have two copies of the given chromosome, there will be two copies of the molecular barcode as opposed to the single barcode provided by the other systems.

While the above-described devices fulfill their respective, particular objectives and requirements, the aforementioned patents do not describe a method and system for tracking specific in situ hybridizations in biological samples using molecular barcodes.

Therefore, a need exists for a new and improved method and system for tracking specific in situ hybridizations in biological samples using molecular barcodes. In this regard, the present invention substantially fulfills this need. In this respect, the method and system according to the present invention substantially departs from the conventional concepts and designs of the prior art, and in doing so provide an apparatus primarily developed for the purpose of tracking specific in situ hybridizations in biological samples using molecular barcodes.

SUMMARY OF THE INVENTION

In view of the foregoing disadvantages inherent in the known types of molecular barcode systems now present in the prior art, the present invention provides an improved method and system to track specific in situ hybridizations in mixed biological samples, and overcomes the above-mentioned disadvantages and drawbacks of the prior art. As such, the general purpose of the present invention, which will be described subsequently in greater detail, is to provide a new and improved method and system to track specific in situ hybridizations in mixed biological samples and method which has all the advantages of the prior art mentioned heretofore and many novel features that result in a method and system to track specific in situ hybridizations in mixed biological samples which is not anticipated, rendered obvious, suggested, or even implied by the prior art, either alone or in any combination thereof.

To attain this, the present invention essentially comprises, in one aspect, a method for tracking specific in situ hybridizations in mixed biological samples using molecular barcodes. The method comprises the steps of:

i) associating specific DNA probes with specific DNA sequences on a specific chromosome within an interphase nuclei;

ii) creating molecular barcodes by selecting said probes which will hybridize to different parts of a genome distinct from the individual chromosomes being investigated; and iii) attaching fluorescent labels, capable of emitting distinct signals, to parts of the said DNA probes such that the final DNA probe generates two to five fluorescent signals, thus creating a distinct molecular barcode wherein the composition of the molecular barcode differs from cell/nucleus to cell/nucleus based on the underlying chromosome being investigated in that particular cell.

In another aspect, the method further involves registering individual locations of the fluorescent signals by excitation of the fluorescent dyes by various lasers, as the cell passes through the flow chamber.

In another aspect, the individual fluorescent signals of the molecular barcode at distinct locations in side the cell are grouped and classified into the respective barcode based on the predetermined configurations in the database.

In yet another aspect, the cells with a specific barcode are electronically sorted into separate bins or baskets for further analysis.

In some embodiments, the fluorescent dye attached to the DNA probe that makes up the barcode, can be aqua 431 dUTP.

In some embodiments, the fluorescent dye attached to the DNA probe that makes up the barcode, can be green 496 dUTP.

In some embodiments, the fluorescent dye attached to the DNA probe that makes up the barcode is Cyanine 3-dUTP.

In some embodiments, the fluorescent dye attached to the DNA probe that makes up the barcode, can be Cyanine 5-dUTP.

In some embodiments, the fluorescent dye attached to the DNA probe that makes up the barcode, can be Red 594 dUTP.

In some embodiments, the molecular barcode can be on chromosome 2.

In some embodiments, the molecular barcode can be on chromosome 1.

In yet another aspect, a composite karyotype can be generated by pooling all individual chromosome profiles being investigated utilizing the molecular barcode as a tracing mechanism for a specific individual chromosome hybridization.

In another aspect, different patient samples can be separated by tracing individual cells from each patient with a distinct molecular barcode.

In another aspect, different molecular assays from the same patient can be sorted out from a single run by tracing individual assays with distinct molecular barcode for each assay.

In another aspect, different individuals exposed to ionizing radiation can be separated from a single run by tracing each individual's cells with distinct molecular barcode.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved method and system for tracking specific in situ hybridizations in biological samples using molecular barcodes that has all of the advantages of the prior art and none of the disadvantages.

It is another object of the present invention to provide a new and improved method and system for tracking specific in situ hybridizations in biological samples using molecular barcodes that may be easily and efficiently manufactured and marketed.

An even further object of the present invention is to provide a new and improved method and system for tracking specific in situ hybridizations in biological samples using molecular barcodes that has a low cost of manufacture with regard to both materials and labor, and which accordingly is then susceptible of low prices of sale to the consuming public, thereby making such method and system for tracking specific in situ hybridizations in biological samples using molecular barcodes economically available to the buying public.

Still another object of the present invention is to provide a new method and system for tracking specific in situ hybridizations in biological samples using molecular barcodes that provides in the apparatuses and methods of the prior art some of the advantages thereof, while simultaneously overcoming some of the disadvantages normally associated therewith.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 depicts in situ hybridization of chromosome 3. A) fluorescent signals depicting the normal pattern. B-C) fluorescent signals depicting a translocation. D1-D2) fluorescent signals depicting the two copies of a molecular barcode with three colors—aqua, red and light green, on chromosome 2.

FIG. 2 depicts in situ hybridization of chromosome 21. A) fluorescent signals depicting the normal pattern. B-C) fluorescent signals depicting a translocation. D1-D2) fluorescent signals depicting the two copies of a molecular barcode with three colors—aqua, red and purple, on chromosome 2.

FIG. 3 depicts in situ hybridization of a target usually involved in rearrangements, mainly translocations, on a given chromosome. A) Fluorescent signals depicting the normal fusion signal pattern. B-C) fluorescent signals depicting the separation of the fusion signals i.e., translocation. D1-D2) fluorescent signals depicting the two copies of a molecular bar code with three colors—aqua, red and purple (sample/patient X), on a chromosome different than the one being investigated in assay A—say chromosome 8.

FIG. 4 depicts in situ hybridization of a target usually involved in rearrangements, mainly translocations, on a given chromosome. A) Fluorescent signals depicting the normal fusion signal pattern. B-C) fluorescent signals depicting the separation of the fusion signals i.e., translocation. D1-D2) fluorescent signals depicting the two copies of a molecular bar code with four colors—aqua, red, blue and purple (sample/patient Y), on a chromosome different than the one being investigated in assay A—say chromosome 8.

FIG. 5 depicts in situ hybridization of a target usually involved in rearrangements, mainly translocations, on a given chromosome. A) Fluorescent signals depicting the normal fusion signal pattern. B-C) fluorescent signals depicting the separation of the fusion signals i.e., translocation. D1-D2) fluorescent signals depicting the two copies of a molecular bar code with two colors—aqua and purple (sample/patient Z), on a chromosome different than the one being investigated in assay A—say chromosome 8.

FIG. 6 depicts in situ hybridization of two targets usually involved in rearrangements, mainly translocations, on the given chromosomes. A) Fluorescent signals depicting the normal signal pattern. B-C) fluorescent signals depicting the splitting of the signal i.e., translocation of the first chromosome being investigated in the assay. D1-D2) fluorescent signals depicting the two copies of a molecular bar code with two colors—aqua and purple (sample/patient X), on a chromosome different than the two chromosomes being investigated in the assay. E-F) Fluorescent signals depicting the normal signal pattern on the second chromosome being investigated in the assay.

FIG. 7 depicts in situ hybridization of two targets usually involved in rearrangements, mainly translocations, on the given chromosomes. A) Fluorescent signals depicting the normal signal pattern. B-C) fluorescent signals depicting the splitting of the signal i.e., translocation of the first chromosome being investigated in the assay. D1-D2) fluorescent signals depicting the two copies of a molecular bar code with three colors—aqua, red and purple (sample/patient Y), on a chromosome different than the two chromosomes being investigated in the assay. E) Fluorescent signals depicting the normal signal pattern on the second chromosome being investigated in the assay. F-G) fluorescent signals depicting the splitting of the signal i.e., translocation of the second chromosome being investigated in the assay.

FIG. 8 depicts in situ hybridization of two targets usually involved in rearrangements, mainly translocations, on the given chromosomes. A-B) Fluorescent signals depicting the normal signal pattern on the first chromosome being investigated in the assay. D1-D2) fluorescent signals depicting the two copies of a molecular bar code with four colors—aqua, red, orange and purple (sample/patient Z), on a chromosome different than the two chromosomes being investigated in the assay. E) Fluorescent signals depicting the normal signal pattern on the second chromosome being investigated in the assay. F-G) fluorescent signals depicting the splitting of the signal i.e., translocation of the second chromosome being investigated in the assay.

DETAILED DESCRIPTION OF THE INVENTION

Figure 1:
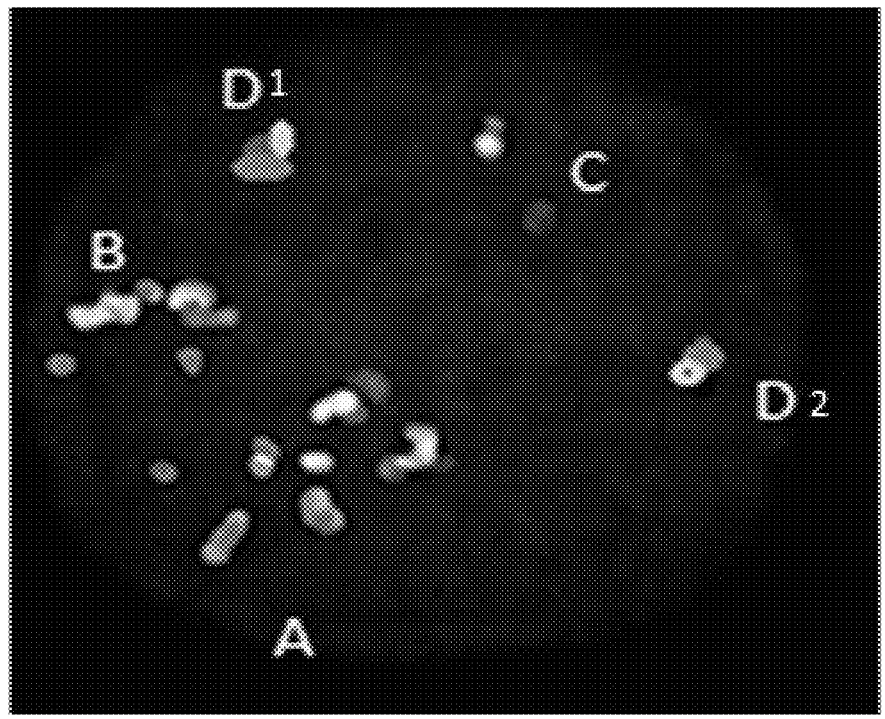
FIGS. 1 and 2 depict exemplary embodiments demonstrating that molecular barcoding can track in situ hybridization of specific individual chromosomes with in the interphase nuclei.
Figure 2:
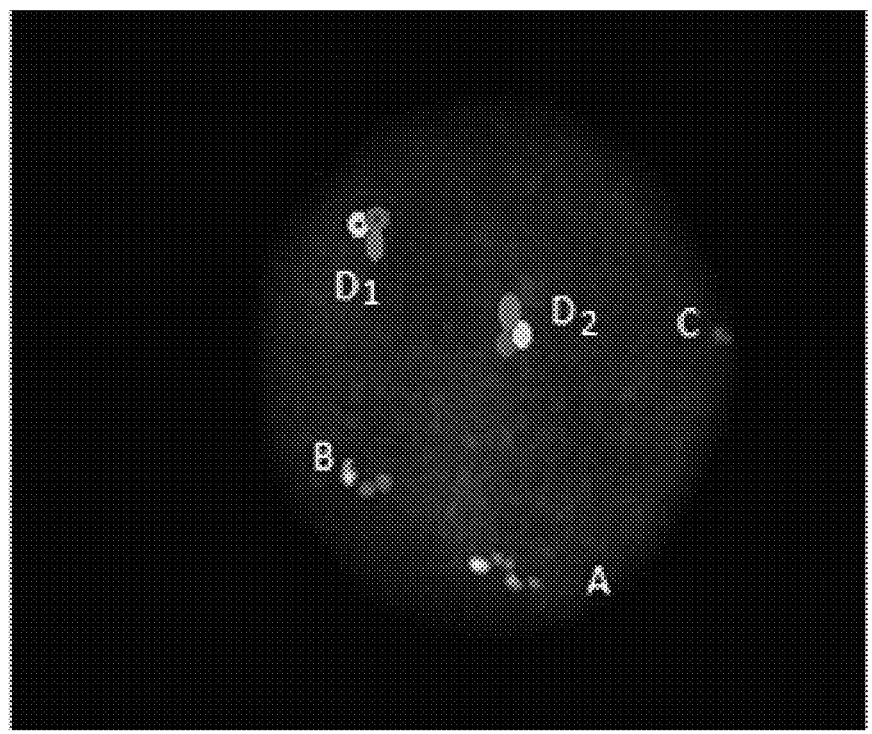

Referring now to the drawings, and particularly to FIGS. 1-8, an embodiment of the method and system for tracking specific in situ hybridizations in biological samples using molecular barcodes of the present invention is shown.

As stated before, Tracking of individual cells which contain specific hybridizations in a mixed sample is very difficult, especially when the mixed sample is processed for high throughput automation through flow cytometers. Yet, to maximize the speed afforded by these high throughput systems, multiple samples have to be mixed in small quantities. The invention claimed here solves this problem.

The current invention enables tracking individual cells with specific hybridizations from the same source, by introducing distinct or unique molecular barcodes into the individual cells. The invention also enables tracking individual samples in a mixed sample, by introducing unique molecular barcodes into the cells in each sample for processing by the high throughput systems.

The claimed invention is an improvement on what currently exists and differs significantly from the prior art. Current molecular barcoding systems use either synthetic macromolecules that do not exist naturally or mRNA probes [1, 2]. Current invention uses molecular barcodes that target naturally existing sequences in the nucleus. Current methods using mRNA barcode don't work when the cells or samples are mixed in suspension for high throughput automation, because the source of the different barcodes in the cells cannot be traced, even though different targets within the cell are identified through the barcode.

Systems that require artificial synthesis of probes are complicated. Systems that are designed for solid surfaces such as for arrays don't address in suspension requirements. Systems designed for tracking various mRNAs don't address the individual tracking of cells.

Present invention specifically addresses the in suspension in situ hybridization protocols and makes it possible to track a mixed sample processed on a high throughput flow cytometer. Since the DNA probes selected for the molecular barcodes are naturally existing sequences on the chromosomes, each cell will have two copies of the molecular barcode as opposed to the single barcode provided by the other systems.

Embodiments of the present invention may include, but not limited to:

1) Make individual molecular barcodes by selecting a DNA probe and labeling it with predetermined barcode. As an example, code 1 can have two fluorescent tags attached to the probes, code 2 may have 3, code 3, 4 tags etc.

2) Hybridize (in suspension) the DNA probes that comprise the tags to the corresponding sample or cell(s) simultaneously with hybridization of the targets in the cells or sample with corresponding DNA probes.

3) Mix individual cells or samples into one sample tube.

4) Process the mixed sample by the high throughput flow cytometer.

5) Track the individual cells or sample through the unique molecular barcode.

Figure 3:
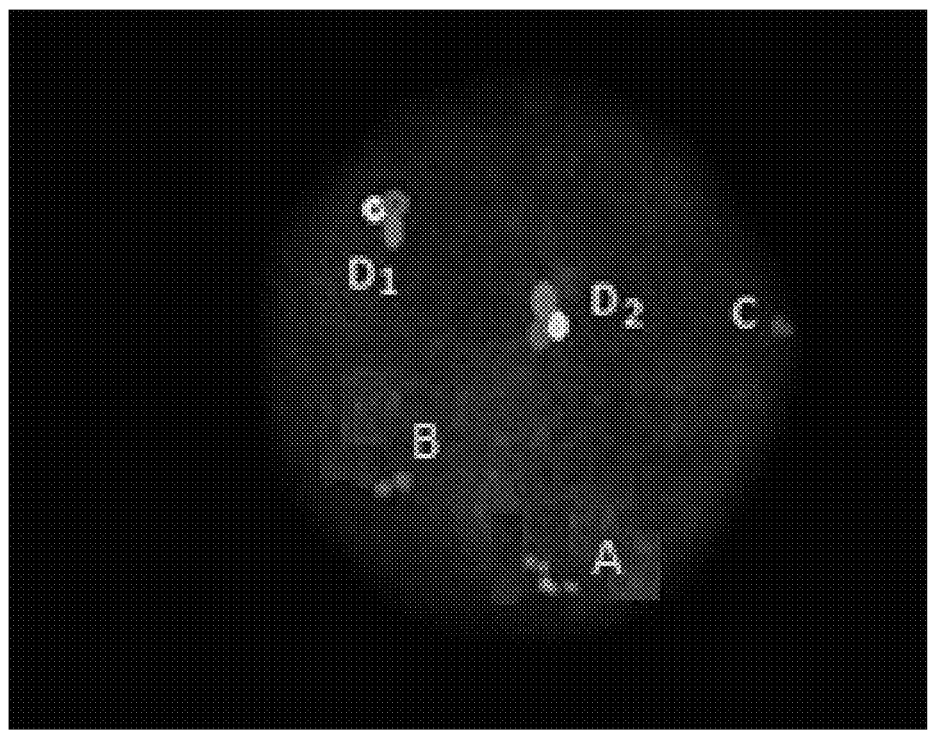
FIGS. 3-5 depict exemplary embodiments demonstrating that molecular barcoding can track in situ hybridization of specific targets on an individual chromosome with in the interphase nuclei in mixed biologic samples, for example from different patients.
Figure 4:
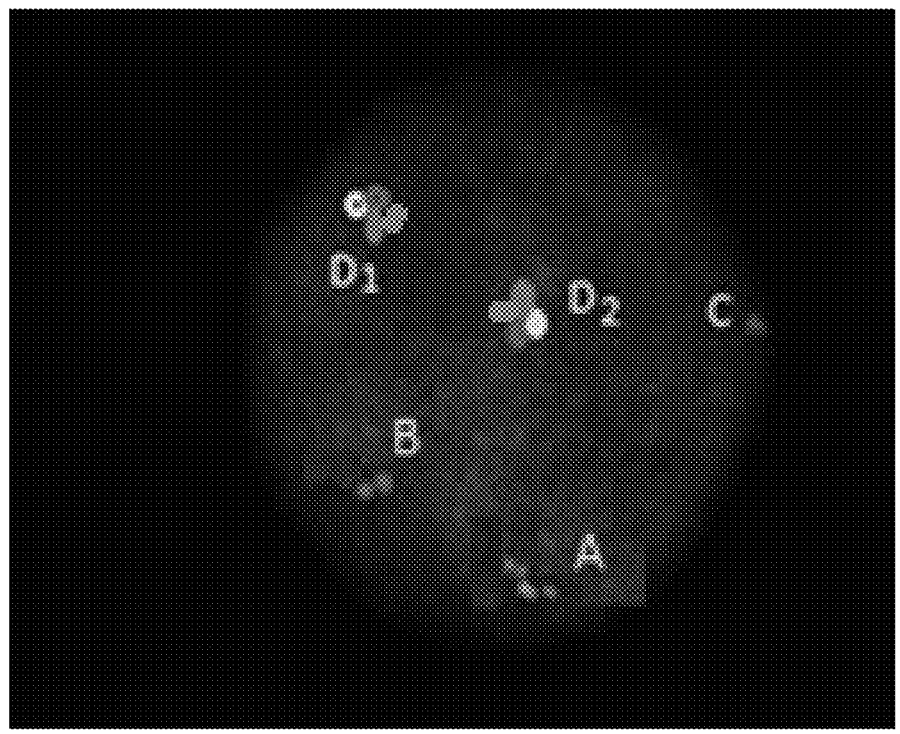
Figure 5:
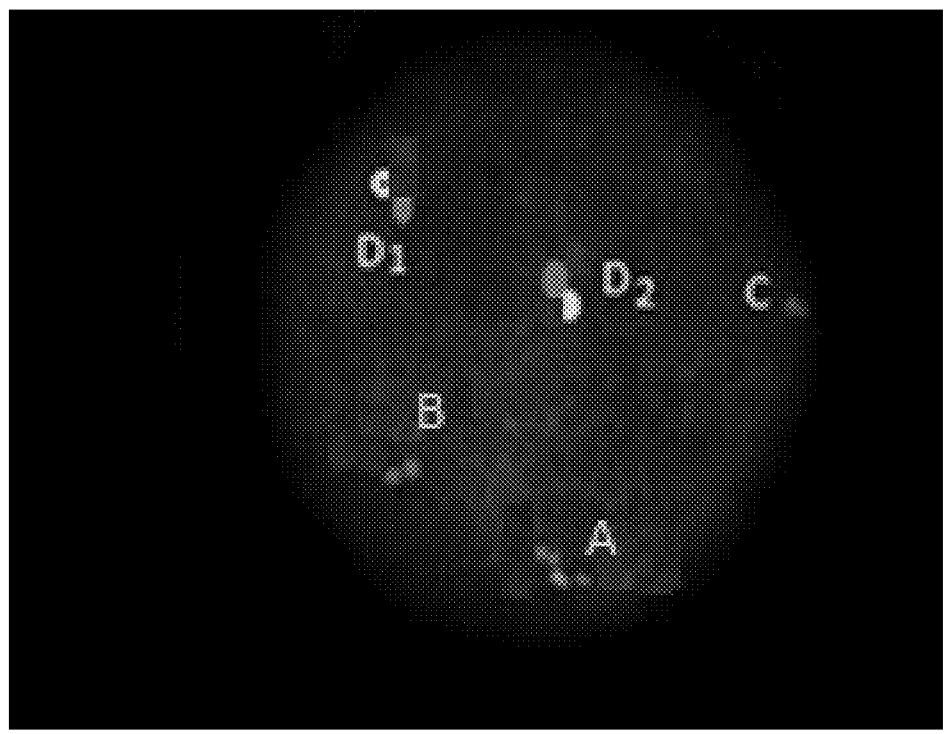
Figure 6:
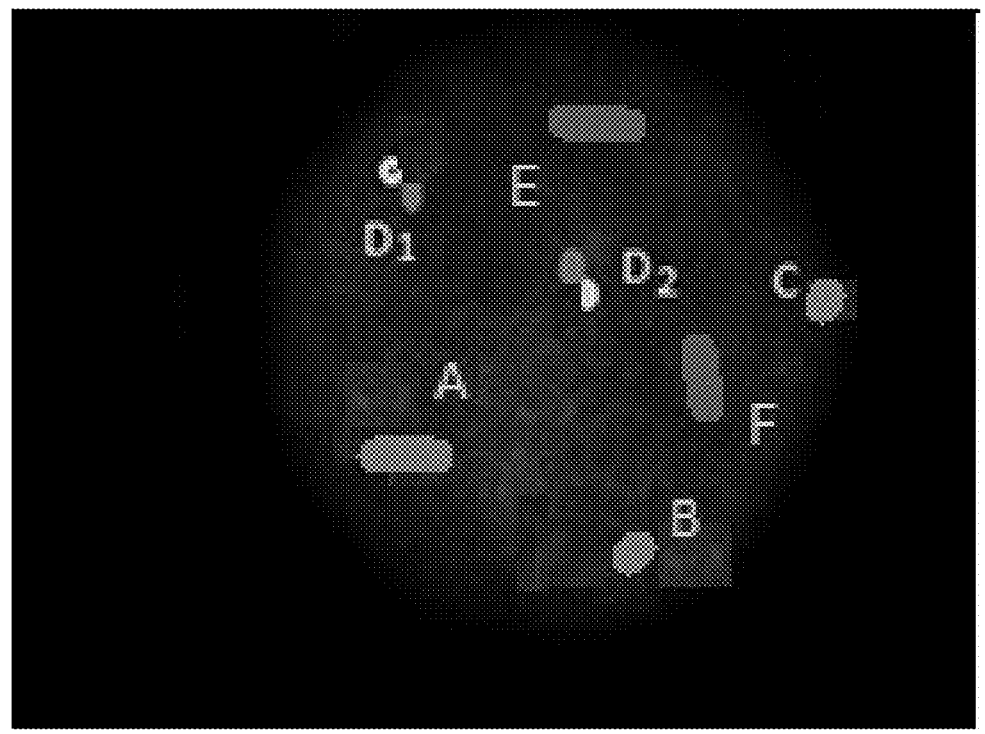
FIGS. 6-8 depict exemplary embodiments demonstrating that molecular barcoding can track in situ hybridization of specific targets on different individual chromosomes with in the interphase nuclei in mixed biologic samples, for example from different patients exposed to ionizing radiation
Figure 7:
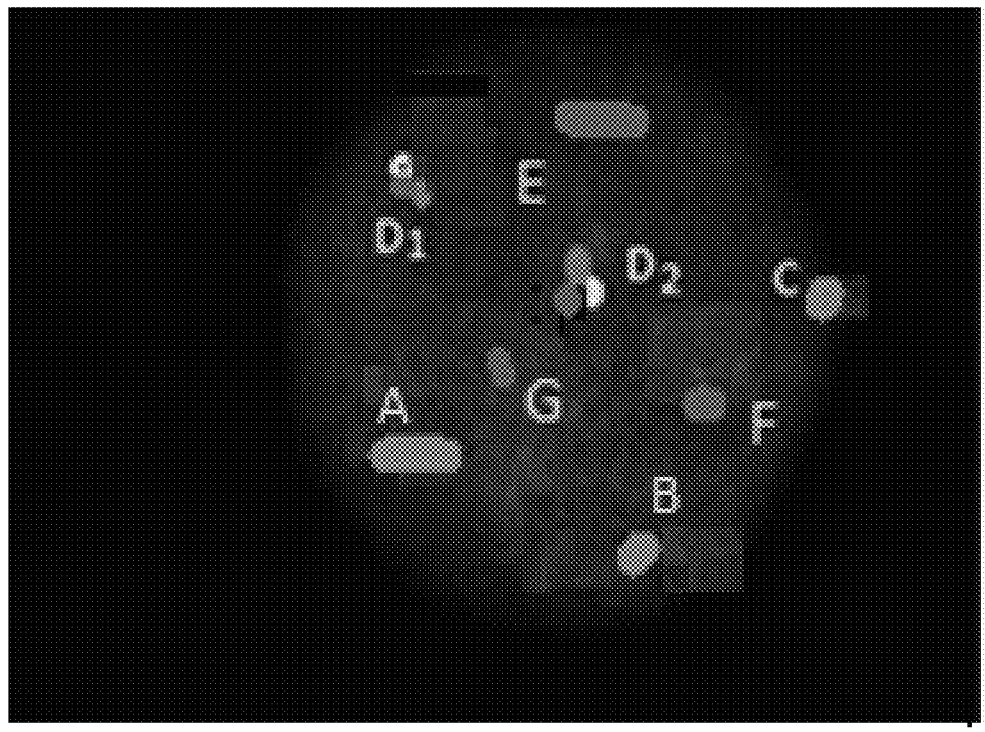
Figure 8:
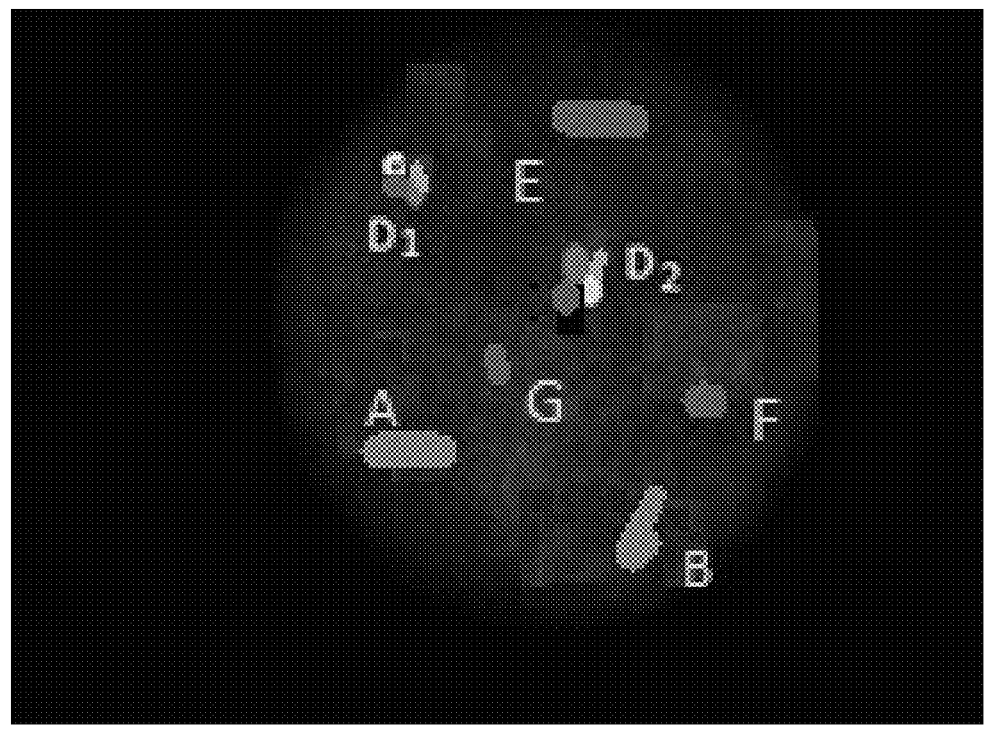

It can be appreciated that drawings may include alternate depictions of in situ hybridization, such as but not limited to:

FIGS. 3-5 can also depict exemplary embodiments demonstrating that molecular barcoding can track in situ hybridization of specific targets on different chromosomes with in the interphase nuclei in mixed biologic samples, from the same patient.

FIG. 3 can also depict in situ hybridization of a target usually involved in rearrangements, mainly translocations, on a given chromosome. A) Fluorescent signals depicting the normal fusion signal pattern B-C) fluorescent signals depicting the separation of the fusion signals i.e., translocation D1-D2) fluorescent signals depicting the two copies of a molecular bar code with three colors—aqua, red and purple (Assay A), on a chromosome different than the one being investigated from the same patient—say chromosome 8.

FIG. 4 can also depict in situ hybridization of a target usually involved in rearrangements, mainly translocations, on a given chromosome. A) Fluorescent signals depicting the normal fusion signal pattern B-C) fluorescent signals depicting the separation of the fusion signals i.e., translocation D1-D2) fluorescent signals depicting the two copies of a molecular bar code with four colors—aqua, red, blue and purple (Assay B), on a chromosome different than the one being investigated from the same patient—say chromosome 14

FIG. 5 can also depict in situ hybridization of a target usually involved in rearrangements, mainly translocations, on a given chromosome. A) Fluorescent signals depicting the normal fusion signal pattern B-C) fluorescent signals depicting the separation of the fusion signals i.e., translocation D1-D2) fluorescent signals depicting the two copies of a molecular bar code with two colors—aqua and purple (Assay C), on a chromosome different than the one being investigated from the same patient—say chromosome 18.

Molecular barcodes needed to uniquely identify cells with specific targets or individual samples with specific targets can be made with step 1 and used in step 2. In step 2, Independent of hybridization of barcodes, the specific targets in cells are simultaneously hybridized with their complimentary probe sets. Step 3 is a pre-requisite for step 4 where the mixed sample is run through the high throughput system. The efficiency gained in step 4 is achieved because of the mixing done in step 3. The characteristics, by which association of the cells with specific targets to unique molecular barcodes is achieved in step 5, are obtained in step 4.

The following is exemplary of how an embodiment of the present invention can work.

By way of an example, a human karyotype can be obtained by studying individual chromosomes in a cell. Molecular ways exist, such as Interphase chromosome profiling (ICP), to establish an individual chromosome profile using DNA probes selected at pre-determined areas along the length of a chromosome. To accomplish this, for each chromosome, individual hybridizations are done in suspension in separate reaction tubes. Using a predetermined molecular barcode, a unique DNA probe with characteristics different from any of the targets on the particular chromosome being profiled, is used so that each cell with that particular chromosome can be traced throughout the processing steps. The DNA probes to generate the molecular barcodes generally comprise either centromere or sub telomere sequences with two to five fluorescent tags. Using a predetermined scheme as outlined in the Table 1 and illustrated in FIGS. 1 and 2, 23 unique molecular barcodes can be prepared and each probe with different barcode can be used simultaneously in hybridizations with the individual chromosome probe sets. The probes used for the barcode are different from the specific chromosome probe sets. This provides the basis for tracing each cell with a particular chromosome profile.

The minimum volume required for high throughput flow cytometers is generally 25 ul or more. The time it takes to process this volume is about 15 min. Whether the volume 25 ul contains 1000 or 1,000,000 cells, the time required for processing is the same i.e., 15 minutes for high resolution chromosome profiling. Therefore, 23 samples each containing 1 ul or more volume of cells with a specific chromosome profile can be combined and processed on a high throughput flow cytometer equipped with multiple lasers to excite all fluorochromes present on the molecular barcode as well as probe sets specific for the chromosome being profiled in individual cells.

As the individual cells are being passed through the flow cytometer, the hybridization characteristics such as the fluorescent color present at the specific targets on the chromosome as well as the barcode will be recorded by the computer. The computer using the predetermined molecular barcode scheme can separate the cells and group them into separate files with each file containing only one type of cell population. For example file 1 can contain only cells with chromosome profile 1 with molecular barcode 1, file 2 with chromosome 2 and barcode 2 etc.

Another example is processing multiple patient samples with a unique barcode assigned to each sample. In this scenario, all the cells in each sample are being investigated for a pre-determined number of targets using specific DNA probes. Each cell in the same sample then gets the same barcode containing different DNA probes than the specific targets being investigated. By combing 23 different samples with 23 different barcodes, the combined sample can be processed on a high throuphput flow cytometer as described above and the computer can sort out each patient sample and generate 23 different files based on the barcode scheme.

The following is exemplary of how a person skilled in the art can use an embodiment of the present invention.

In order to generate a human karyotype by interphase chromosome profiling, in an automated way by using high throughput flow cytometers, a person skilled in the art may perform the following tasks:

1) Design the DNA probes with unique molecular barcodes as per the guidance in the present invention.

2) Perform in suspension in situ hybridization of both molecular barcode and specific target DNA probes simultaneously to the cells or samples of interest.

3) Mix the hybridizations into a single sample.

4) Process the sample through a high throughput flow cytometer.

5) Track the individual cells or samples through computer identification of the barcodes.

A person skilled in the art could also use this invention to track multiple patient samples processed in a single run on a mixed sample. For this application, one would choose a particular assay designed for a number of specified targets in a cell and apply unique barcodes to each patient sample and mix the samples after the in suspension hybridization and finally run on the flow cytometer.

Another application would be to use this invention for multiple different assays. For example in the mixed sample, some samples may be related to assay 1, others assay 2 etc.

Yet another application involves the use of part of a sample for part of a single assay such that combining multiple parts of a given sample will result in a single assay.

As can be seen from the above description, a user skilled in the art will have flexibility in designing a single run with various combinations.

Molecular Barcode Characteristics:

As described herein, each probe contains a plurality of DNA fragments tagged with two, three, four or five fluorochromes. The computer will look for the hybridization signals and when an area matches with the predetermined barcode combinations, it assigns that cell a specific barcode. Since the barcodes are landmarks on a chromosome, and each cell has two chromosomes, there will be two identical barcodes.

How to Make the Invention:

Bacterial Artificial Chromosomes (BAC) to make the necessary DNA probes are commercially available for those skilled in the art. The sources are listed herein, but not limited to: 1) National Center for Biotechnology Information; 2) Open Biosystem; and 3) BACPAC Services.

The fluorescent labels to attach to the probes are commercially available at Enzo life sciences—Enzo Life Sciences, Inc. These can include fluorochromes such as Fluorescein, Tex. Red, Coumarin, Cyanine3, Cyanine5 and the like. Those skilled in the art would know to select the fluorochromes with different excitation and emission spectral characteristics. Table 1 lists a barcode set consisting 23 unique barcodes with different fluorochrome combinations that can be used for this invention.

TABLE 1

| Chromosome | Aqua | Cy5 | Green | Cy3 | Red | A | C | G | C | R |
|---|---|---|---|---|---|---|---|---|---|---|
| 1 | x | xx | xx | | | x | x | | | |
| 2 | | x | xx | xx | | | x | x | | |
| 3 | | | x | xx | xx | | x | x | | |
| 4 | x | xx | | xx | | | | | x | x |
| 5 | x | xx | | | xx | x | | x | | |
| 6 | | xx | x | | xx | x | | | x | |
| 7 | x | | xx | | xx | x | | | | x |
| 8 | | x | | xx | xx | x | x | | | |
| 9 | x | | | xx | xx | x | | | | x |
| 10 | x | | xx | xx | | | | x | | x |
| 11 | x | | | x | | x | x | | | x |
| 12 | x | | | | x | x | x | x | | |
| 13 | | x | | x | | | x | x | | x |
| 14 | | x | | | x | | x | x | x | |
| 15 | xx | xx | xx | xx | | | x | x | x | |
| 16 | | xx | xx | xx | xx | x | | x | x | x |
| 17 | xx | xx | | xx | xx | | x | x | | x |
| 18 | xx | | xx | xx | xx | x | x | | | x |
| 19 | xx | xx | xx | | xx | x | x | x | | |
| 20 | x | | x | | | x | | x | x | |
| 21 | | x | x | | | | x | | x | x |
| 22 | x | x | | | | x | x | x | x | |
| XY/23 | xx | xx | xx | xx | xx | x | x | x | x | x |

To barcode individual chromosome hybridizations (1-22, XY), the combinations in the table under the headings Aqua, Cy5, Green, Cy3, Red can be used. For barcoding individual specimens the combinations on the right side of the table under the letter headings A, C, G, C, R can be used. The colors of the letters indicate the barcode color combinations. X in the table indicates unshared and XX indicates shared colors among DNA fragments in the molecular barcode.

Fluorescence in situ hybridization (FISH) is a well-established technique and protocols for in suspension hybridization to be used in this invention, are available for those skilled in the art, in the public domain [3]. High throughput flow cytometers are commercially available from Amnis Corporation. Amnis Corporation also has developed protocols for in suspension FISH and these protocols are available to those skilled in the art [4].

To successfully track individual cells or samples in a mixed sample processed on a high throughput flow cytometer, it is essential to 1) make distinct molecular barcodes 2) hybridize the probes with unique barcodes with cells in separate in suspension in situ hybridization vials 3) mix the individual hybridizations into a single sample. By following this invention, those skilled in the art will realize the extraordinary potential afforded by the high throughput flow cytometry systems available in the market.

The fluorescent labels used for the molecular barcode can be interchanged with non-fluorescent labels such as biotin, degoxigenin etc. These ligands can be detected through their affinity for substances such as avidin or specific antibodies raised against these ligands. This is an indirect two-step process where the DNA probe is tagged with a non-fluorescent ligand first. Then it is incubated with an antibody conjugated to an enzyme such as alkaline phosphatase, horseradish peroxidase and the like. The final detection of the probe hybridization takes place when the enzyme specifically reacts with a substrate to produce a color precipitate at the site of hybridization [5]. This colorimetric detection also accomplishes the same as the fluorescence based system for the purpose of using this invention. The number of different molecular barcodes that can be generated then depends on the number of available enzymes and substrates. By mixing different amounts of DNA probe fragments, it should be possible to generate hybrid colors at the site of hybridization. For example a green produced from Alkaline Phosphatase reaction and a red produced from a Peroxidase reaction, will produce yellow after being mixed at the same site of hybridization. The colors are detected through the bright field channel in the flow cytometer as compared to the fluorescent channels described for the fluorescence system.

EXAMPLES

Example 1

Tracing Individual Chromosome Hybridizations and Generation of a Human Karyotype In one embodiment, a human karyotype can be obtained by studying individual chromosomes in a cell. Molecular genetic technologies exist, such as Interphase chromosome profiling (ICP), [6, 7] to establish an individual chromosome profile using DNA probes selected at pre-determined areas along the length of a chromosome. To accomplish this, for each chromosome, individual hybridizations are done in suspension in separate reaction tubes. Using a predetermined molecular barcode, a unique DNA probe with characteristics different from any of the targets on the particular chromosome being profiled, is used so that each cell with that particular chromosome can be traced throughout the processing steps. The DNA probes to generate the molecular barcodes generally comprise either centromere or sub telomere sequences with two to five fluorescent labels. Using a predetermined scheme as outlined in Table 1, and illustrated in FIGS. 1 and 2, twenty-three (23) unique molecular barcodes can be generated and each probe with different barcode can be used simultaneously in hybridizations with the individual chromosome probe sets. The probes used for the barcode are different from the specific chromosome probe sets. For example, to generate a chromosome 1 profile one would use probes from chromosome 2 to create a molecular barcode; for chromosome 2 profiling use probes on chromosome 1, and for the rest of the chromosomes' profiling use chromosome 2 probes to generate the molecular barcode. This provides the basis for tracing each cell with a particular chromosome profile.

The minimum volume required for high throughput flow cytometers is generally 25 ul or more. The time it takes to process this volume is about 15 min. Whether the volume 25 ul contains 1000 or 1,000,000 cells, the time required for processing is the same i.e., 15 minutes for high resolution chromosome profiling. Therefore, 23 samples each containing 1 ul or more volume of cells with a specific chromosome profile can be combined and processed on a high throughput flow cytometer equipped with multiple lasers to excite all fluorochromes present on the molecular barcode as well as probe sets specific for the chromosome being profiled in individual cells.

As the individual cells are being passed through the flow cytometer, the hybridization characteristics such as the fluorescent color present at the specific targets on the chromosome as well as the barcode will be recorded by the computer. The computer using the predetermined molecular barcode scheme can separate the cells and group them into separate files with each file containing only one type of cell population. For example file 1 can contain only cells with chromosome profile 1 with molecular barcode 1, file 2 with chromosome 2 and barcode 2 etc.

Example 2

Tracking Multiple Patients for a Single Clinical Assay

In another embodiment, multiple patient samples with a unique barcode assigned to each sample can be processed in a single run on a high throughput flow cytometer. In this scenario, all the cells in each different sample are being investigated for a pre-determined number of targets using specific DNA probes as in a specific assay. Each cell in the same sample then gets the same barcode containing different DNA probes than the specific targets being investigated in the said assay. By combing 23 different patient samples with a distinct barcode for each sample, the combined sample can be processed on a high throughput flow cytometer as described above and the computer can sort out each patient sample and generate 23 different files based on the predetermined barcode scheme.

Example 3

Tracking Multiple Assays from a Single Patient

In yet another embodiment, multiple assays from a given patient with each assayed cell with a specific molecular barcode can be processed in a single run on a high throughput flow cytometer. In this scenario, all the cells with a specific assay investigated for a pre-determined number of targets using specific DNA probes will receive a distinct molecular barcode than the cells with a different assay, for example. By combing 23 different assayed samples each with a distinct barcode, the combined sample from a given patient can be processed on a high throughput flow cytometer as described above and the computer can sort out each assayed sample and generate 23 different files based on the predetermined barcode scheme.

Example 4

Tracking Individual Patients Exposed to Ionizing Radiation in a Single Chromosome Assay In another embodiment, multiple patient samples (those exposed to ionizing radiation) with a unique barcode assigned to each sample can be processed in a single run on a high throughput flow cytometer. In this scenario, all the cells in each different sample are being investigated for a pre-determined number of targets using specific DNA probes as in a specific assay. Each cell in the same sample then gets the same barcode containing different DNA probes than the specific targets being investigated in the said assay. By combing 23 different patient samples each with a distinct barcode, the combined sample can be processed on a high throughput flow cytometer and the computer can sort out each exposed patient sample and generate 23 different files based on the predetermined barcode scheme.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in the embodiments of the present invention. Still further variations and alternate elements will be apparent to those skilled in the art. Among these variations without limitation, are the specific number of fluorochromes in a molecular barcode or the specific number of assays or the specific number of patient samples for a single assay. Various embodiments of the invention can include or exclude any of these variations or elements.

Furthermore, numerous references have been made to patents and printed publications throughout this specification. Each of the above cited references are herein individually incorporated by reference in their entirety.

Finally, it is to be understood that the embodiments of the invention disclosed herein are illustrative of the principles of the present invention. Other modifications that can be employed can be within the scope of the invention. Therefore, by way of example, but not of limitation, alternative configurations of the present invention can be utilized in accordance with the teachings herein. Accordingly, embodiments of the present invention are not limited to that precisely as shown and described.

While embodiments of the method and system for tracking specific in situ hybridizations in biological samples using molecular barcodes have been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

REFERENCES

Sample tracking using molecular barcodes. Patent Application WO 2003052101 A1.
Molecular indicia of cellular constituents and resolving the sample by super-resolution technologies in single cells. Patent Application US 20120142014 A1.
Timm E A Jrl, Stewart C C. Fluorescent in situ hybridization en suspension (FISHES) using digoxigenin-labeled probes and flow cytometry Biotechniques. 1992 March; 12(3):362-7.
Minderman H, Humphrey K and Arcadi J K et al., Image Cytometry-based detection of aneuploidy by fluorescence in situ hybridization in suspension. Cytometry Part A. 81A:776-784, 2012.
Von Rooijen N and Kors N Double immunoenzyme cytochemistry for simultaneous detection of antigen specificity and (sub)class of antibodies. J Histochem Cytochem 1985 pp 175-78.
Method and apparatus for chromosome profiling U.S. Pat. No. 8,574,836.
Method and apparatus for chromosome profiling U.S. Pat. No. 7,943,304.

What is claimed as being new and desired to be protected by Letters Patent of the United States is as follows:

1. A method for tracking specific in situ hybridizations in multiple different biological samples, said method comprising steps of:
   a) providing multiple different biological samples, each of said different multiple biological samples being obtained from at least one patient for at least one clinical assay or from at least one individual exposed to radiation;
   b) obtaining a plurality of different sets of DNA probes, wherein each set of said plurality of different sets of DNA probes comprises different probes which specifically hybridize to different parts of one of different chromosomes and contain two to five different fluorescent labels, and wherein each set of said plurality of different sets of DNA probes specifically hybridizes to a different chromosome of said different chromosomes;
   c) for each of said multiple different biological samples, separately performing fluorescence in situ hybridizations in suspension of each of said multiple different biological samples by simultaneously hybridizing:
      selected sets of probes from said plurality of different sets of DNA probes to selected chromosomes of said different chromosomes in said suspension of each of said multiple different biological samples such that two to five differential fluorescent color bands are produced on each of the selected chromosomes of said different chromosomes, wherein the selected sets of probes and the selected chromosomes used for performing said fluorescence in situ hybridizations in suspension of each of said multiple different biological samples are different, thereby creating a plurality of different molecular barcodes on the selected chromosomes of said different chromosomes of each of said multiple different biological samples, wherein each of said plurality of different molecular barcodes is a fluorescent pattern generated from the two to five differential fluorescent color bands on one of the selected chromosomes of said different chromosomes of each of said multiple different biological samples;
   d) forming a fluorescent labeled mixed suspension by mixing the cells from suspension of each of said multiple different biological samples after step c) and creating a unique sample barcode for each of said multiple different biological samples, wherein the sample barcode is a combination of the plurality of different molecular barcodes on the selected chromosomes of said different chromosomes in each of said multiple different biological samples and is different in each of said multiple different biological samples but is identical in each cell of each of said multiple different biological samples;
   e) passing the cells from said fluorescent labeled mixed suspension through a flow chamber of a high throughput flow cytometer, said high throughput flow cytometer reads distinct fluorescent signals generated from said sample barcode from each of said multiple different biological samples; and
   f) tracking said specific in situ hybridizations in said multiple different biological samples by detecting said distinct fluorescent signals generated from said sample barcode from each of said multiple different biological samples using said high throughput flow cytometer.

2. The method of claim 1, further comprising registering individual locations of said distinct fluorescent signals on each of the selected chromosomes of said different chromosomes in each of said multiple different biological samples by excitation of fluorescent labels from said two to five differential fluorescent color bands on each of the selected chromosomes of said different chromosomes in each of said multiple different biological samples by lasers, as the cells from said fluorescent labeled mixed suspension pass through said flow chamber of said high throughput flow cytometer.

3. The method of claim 1, wherein said different fluorescent labels are selected from the group consisting of aqua 431 dUTP, green 496 dUTP, Cyanine 3-dUTP, Cyanine 5-dUTP, Red 594 dUTP, and analogs or derivatives thereof.

4. The method of claim 1, wherein a computer of said high throughput flow cytometer records said distinct fluorescent signals on each of the selected chromosomes of said different chromosomes in each of said multiple different biological samples, as the cells from said fluorescent labeled mixed suspension pass through said flow chamber of said high throughput flow cytometer.

5. The method of claim 4, wherein said computer separates the cells from said fluorescent labeled mixed suspension and group them into separate computer files with each of said computer files containing only one type of the cells using a predetermined molecular barcode scheme.

6. The method of claim 1, wherein one of said plurality of different molecular barcodes is located on one of said different chromosomes selected from the group consisting of chromosome 1 and chromosome 2.

7. The method of claim 1, wherein said plurality of different molecular barcodes are used to produce a complete karyotype, by combining individual interphase chromosome profiles, when said multiple different biological samples are from a human.

8. The method of claim 1, wherein origins of said multiple different biological samples are selected from the group consisting of amniotic fluid, chorionic villi, peripheral blood, plural fluid, bone marrow, and tumor tissue.

9. The method of claim 1, wherein said at least one patient is different patients.

10. The method of claim 1, wherein said at least one clinical assay is different clinical assays.

11. The method of claim 1, wherein said at least one individual exposed to radiation is different individuals exposed to said ionizing radiation.

* * * * *